US007915249B2

(12) United States Patent
Cid-Núñez et al.

(10) Patent No.: US 7,915,249 B2
(45) Date of Patent: Mar. 29, 2011

(54) HETEROCYCLIC TETRACYCLIC TETRAHYDROFURAN DERIVATIVES AS 5HT$_2$ INHIBITORS IN THE TREATMENT OF CNS DISORDERS

(75) Inventors: José Maria Cid-Núñez, Toledo (ES); Antonius Adrianus Hendrikus Petrus Megens, Beerse (BE); Andrés Avelino Trabanco-Suárez, Olias del Rey (ES)

(73) Assignee: Janssen Pharmaceutical NV, Beerse (BE)

( * ) Notice: Subject to any disclaimer, the term of this patent is extended or adjusted under 35 U.S.C. 154(b) by 431 days.

(21) Appl. No.: 11/814,432

(22) PCT Filed: Jan. 25, 2006

(86) PCT No.: PCT/EP2006/050444
§ 371 (c)(1),
(2), (4) Date: Jul. 20, 2007

(87) PCT Pub. No.: WO2006/079637
PCT Pub. Date: Aug. 3, 2006

(65) Prior Publication Data
US 2008/0108599 A1    May 8, 2008

(30) Foreign Application Priority Data
Jan. 27, 2005   (EP) .................................... 05100547

(51) Int. Cl.
| | | |
|---|---|---|
| *A61K 31/397* | (2006.01) | |
| *A61K 31/00* | (2006.01) | |
| *A61K 31/55* | (2006.01) | |
| *A61K 31/497* | (2006.01) | |
| *A61K 31/47* | (2006.01) | |
| *A61K 31/44* | (2006.01) | |
| *A61K 31/40* | (2006.01) | |
| *A61K 31/335* | (2006.01) | |
| *C07D 405/00* | (2006.01) | |
| *C07D 409/00* | (2006.01) | |
| *C07D 285/30* | (2006.01) | |
| *C07D 295/00* | (2006.01) | |
| *C07D 295/02* | (2006.01) | |
| *C07D 217/00* | (2006.01) | |
| *C07D 417/00* | (2006.01) | |
| *C07D 419/00* | (2006.01) | |
| *C07D 211/02* | (2006.01) | |
| *C07D 209/44* | (2006.01) | |
| *C07D 313/20* | (2006.01) | |
| *A01N 43/00* | (2006.01) | |
| *A01N 43/42* | (2006.01) | |
| *A01N 43/40* | (2006.01) | |
| *A01N 43/38* | (2006.01) | |
| *A01N 43/36* | (2006.01) | |
| *A01N 43/02* | (2006.01) | |
| *A01N 43/22* | (2006.01) | |

(52) U.S. Cl. ......... 514/210.16; 514/210.19; 514/211.01; 514/213.01; 514/217.03; 514/252.13; 514/307; 514/338; 514/416; 514/422; 514/431; 514/450; 540/596; 544/106; 544/375; 546/139; 546/197; 546/202; 548/515; 548/526; 549/12; 549/354

(58) Field of Classification Search ....................... None
See application file for complete search history.

(56) References Cited

U.S. PATENT DOCUMENTS
4,031,225 A   6/1977 Bastian et al.

FOREIGN PATENT DOCUMENTS
| CS | 200271 B1 | 12/1982 |
|---|---|---|
| CS | 217949 B1 | 12/1984 |
| DE | 2625642 A1 | 1/1977 |
| PL | 158223 B1 | 8/1992 |
| WO | 97/38991 A | 10/1997 |
| WO | 97/39001 A | 10/1997 |
| WO | 99/19317 A1 | 4/1999 |
| WO | 03/040122 A1 | 5/2003 |
| WO | 03/048146 A1 | 6/2003 |

OTHER PUBLICATIONS
International Search Report, dated May 8, 2006, 2 pages.
(Continued)

*Primary Examiner* — Noble Jarrell

(57) ABSTRACT

This invention concerns novel substituted heterocyclic tetracyclic tetrahydrofuran derivatives with binding affinities towards serotonin receptors, in particular 5-HT$_{2A}$ and 5-HT$_{2C}$ receptors, and towards dopamine receptors, in particular dopamine D$_2$ receptors and with norepinephrine reuptake inhibition properties, pharmaceutical compositions comprising the compounds according to the invention, the use thereof as a medicine, in particular for the prevention and/or treatment of a range of psychiatric and neurological disorders, in particular certain psychotic, cardiovascular and gastrokinetic disorders and processes for their production.
The compounds according to the invention can be represented by general Formula (I)

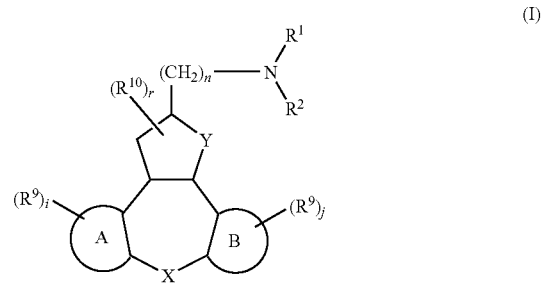

and comprises also the pharmaceutically acceptable acid or base addition salts thereof, the stereochemically isomeric forms thereof, the N-oxide form thereof and prodrugs thereof, wherein all substituents are defined as in Claim 1.

7 Claims, No Drawings

OTHER PUBLICATIONS

Lohse et al., "New synthesis of oxcarbazepine via remote metalation of protected N-o-tolyl-anthranilamide derivatives.", Tetrahedron Letters, 2001, pp. 385-389, vol. 42(3).

Majchrzak, M., "Addition of 3-thienyllithium to phthalic anhydride: A simple method for the synthesis of 9,10-dihydro-4H-benzo[4,5]cyclohepta[1,2-b]thiophen-10-one.", Journal of Heterocyclic Chemistry, 1985, pp. 1203-1204, vol. 22(5).

Majchrzak, M., "Synthesis of 2-(1-methyl-4-piperylid-3-ene)-9,10-dihydro-4H-benzo[4,5]-cyclohepta[1,2-b]thiophen-10-one, a new potential antiasthmatic analogue of zaditene.", Journal of Heterocyclic Chemistry, 1985, pp. 1205-1206, vol. 22(5).

Meert et al., "Partial and complete blockade of 5-hydroxytrytophan (5-HTP)-induced head twitches in the rat: A study of ritanserin (R 55 667), risperidone (R 64 766), and related compounds.", Drug Dev. Res., 1988, pp. 237-244, 13(4).

Monkovic et al., "Substituted tetrahydrofurfurylamines as potential antidepressants.", J. Med. Chem., Apr. 1973, pp. 403-407, vol. 16(4).

Protiva el al., Collection of Czechoslovak Chemical Communications, 1969, pp. 468-478, vol. 34(2).

Stella et al., "Prodrugs. Do they have advantages in clinical practice?", Drugs, 1985, pp. 455-473, vol. 29.

HETEROCYCLIC TETRACYCLIC TETRAHYDROFURAN DERIVATIVES AS 5HT$_2$ INHIBITORS IN THE TREATMENT OF CNS DISORDERS

CROSS REFERENCE TO RELATED APPLICATIONS

This application is the national stage of Application No. PCT/EP2006/050444, filed 25 Jan. 2006, which application claims priority from EP 05100547.8 filed 27 Jan. 2005, which are hereby incorporated by reference herein.

FIELD OF THE INVENTION

This invention concerns novel substituted heterocyclic tetracyclic tetrahydrofuran derivatives with binding affinities towards serotonin receptors, in particular 5-HT$_{2A}$ and 5-HT$_{2C}$ receptors, and towards dopamine receptors, in particular dopamine D$_2$ receptors and with norepinephrine reuptake inhibition properties, pharmaceutical compositions comprising the compounds according to the invention, the use thereof as a medicine, in particular for the prevention and/or treatment of a range of psychiatric and neurological disorders, in particular certain psychotic, cardiovascular and gastrokinetic disorders and processes for their production.

BACKGROUND PRIOR ART

WO 97/38991, published Oct. 23, 1997 (Janssen Pharmaceutica N.V.) discloses substituted tetracyclic tetrahydrofuran derivatives that may be used as therapeutic agents in the treatment or prevention of CNS disorders, cardiovascular disorders or gastrointestinal disorders. In particular, the compounds show affinity for the serotonin 5-HT$_2$ receptors, particularly for the 5-HT$_{2A}$ and 5-HT$_{2C}$-receptors.

WO 99/19317, published Apr. 22, 1999 (Janssen Pharmaceutica N.V.) discloses substituted tetracyclic tetrahydrofuran derivatives with a specific halogen substitution pattern on the dibenzoazepine, dibenzooxepine, dibenzothiepine or dibenzosuberane ring. The compounds are useful in the treatment or prevention of CNS disorders, cardiovascular disorders or gastrointestinal disorders and show a faster onset of action over the compounds as disclosed in WO 97/38991.

Both WO 03/048146, published Jun. 12, 2003 (Janssen Pharmaceutica N.V.) and WO 03/048147, published Jun. 12, 2003 (Janssen Pharmaceutica N.V.) disclose processes for the preparation of each of the 4 diastereomers of cis-, respectively transfused 3,3a,8,12b-tetrahydro-2H-dibenzo[3,4:6,7]cyclohepta[1,2-b]furan derivatives in a stereochemically pure form from a single enantiomerically pure precursor.

WO 03/040122, published May 15, 2003 (Janssen Pharmaceutica N.V.) discloses mandelate salts of the compounds according to WO 97/38991 and WO 99/19317. Said salts were surprisingly found to be more stable at enhanced temperature and relative humidity than the compounds disclosed in WO 97/38991 and WO 99/19317.

Further should be mentioned WP 97/39001, published Oct. 23, 1997 (Janssen Pharmaceutica N.V.), which discloses heterocyclic tetracyclic isoxazolidine derivatives and which show affinity for the 5-HT$_2$ receptors.

DESCRIPTION OF THE INVENTION

It is the object of the present invention to provide novel heterocyclic analogues of the tetracyclic tetrahydrofuran derivatives of WO 97/38991 and WO 99/19317, which have been found to have surprising advantages over the latter compounds in regard to improved affinity for the 5-HT$_{2A}$ and 5-HT$_{2C}$ receptors and the norepinephrine reuptake transporters.

Surprisingly, the compounds of the present invention also showed a high to moderate dopamine D$_2$ activity, making the compounds interesting for the treatment of dopamine regulated conditions, in particular schizophrenia. None of the compounds of the prior art was documented to exhibit said dopamine D$_2$ activity and none of the prior art documents has pointed out how to introduce said activity in a molecule that has affinity for the 5-HT$_{2A}$ and 5-HT$_{2C}$ receptors, while retaining said affinity for the 5-HT$_{2A}$ and 5-HT$_{2C}$ receptors.

This goal is achieved by the present novel compounds according to Formula (I)

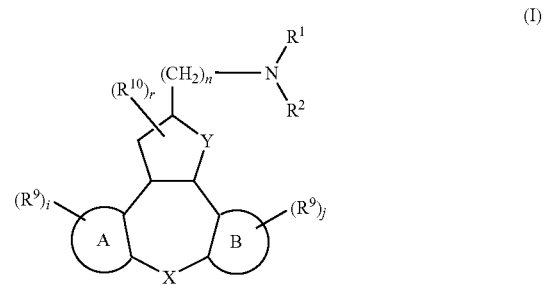

(I)

an N-oxide form, a pharmaceutically acceptable addition salt or a stereochemically isomeric form thereof, wherein:

n is an integer, equal to zero; 1; 2; 3; 4; 5 or 6;
i, j are integers, independently from each other, equal to zero; 1; 2; 3 or 4;
r is an integer, equal to zero; 1; 2; 3 or 4;
R$^1$ and R$^2$ each independently from each other, are hydrogen; alkylcarbonyl; alkyl; alkyloxyalkyl; alkylcarbonyloxyalkyl; alkyloxycarbonylalkyl; arylalkyl; arylcarbonyl; alkyloxycarbonyl; aryloxycarbonyl; arylalkylcarbonyl; alkyloxycarbonylalkylcarbonyl; mono- or di(alkyl)aminocarbonyl; mono- or di(aryl)aminocarbonyl; mono- or di(arylalkyl)aminocarbonyl; mono- or di(alkyloxycarbonylalkyl)aminocarbonyl; alkylsulphonyl; arylsulphonyl; arylalkylsulphonyl; mono- or di(alkyl)aminothiocarbonyl; mono- or di(aryl)aminothiocarbonyl; mono- or di(arylalkyl)aminothiocarbonyl; mono-, di- or tri(alkyl)amidino; mono-, di- or tri(aryl)amidino and mono-, di- or tri(arylalkyl)amidino; or R$^1$ and R$^2$ taken together with the nitrogen atom to which they are attached may form a radical of Formula:

(a-1)

(a-2)

-continued

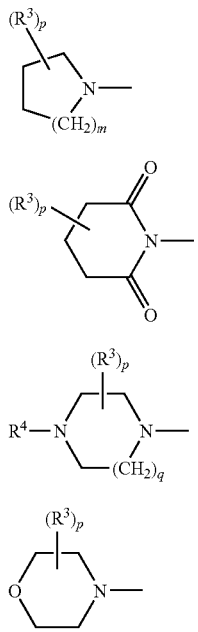

wherein:
p is an integer equal to zero; 1; 2; 3 or 4;
q is an integer equal to 1 or 2;
m is an integer equal to zero; 1; 2 or 3;
each $R^3$ independently from each other, is selected from the group of halo; hydroxy; cyano; alkyl; alkyloxyalkyl; aryloxyalkyl; mono- or di(alkyl)aminoalkyl; hydroxycarbonylalkyl; alkyloxycarbonylalkyl; mono- or di(alkyl)aminocarbonylalkyl; mono- or di(aryl)aminocarbonylalkyl; mono- or di(alkyl)aminocarbonyloxyalkyl; alkyloxycarbonyloxyalkyl; arylaminocarbonyloxyalkyl; arylalkylaminocarbonyloxyalkyl; aryl; alkyloxy; aryloxy; alkylcarbonyloxy arylcarbonyloxy; arylalkylcarbonyloxy; alkylcarbonyl; arylcarbonyl; aryloxycarbonyl; hydroxycarbonyl; alkyloxycarbonyl; mono- or di-alkylamino; alkylcarbonylamino; arylalkylcarbonylamino; arylcarbonylamino; alkyloxycarbonylamino; aminocarbonylamino; mono- or di(arylalkyl)aminocarbonylamino; alkylsulphonylalkylaminocarbonylamino; or
two $R^3$-radicals may form together a bivalent radical
—$CR^5R^5$—$CR^5R^5$—O— (b-1)
—O—$CR^5R^5$—$CR^5R^5$— (b-2)
—O—$CR^5R^5$—$CR^5R^5$—O— (b-3)
—O—$CR^5R^5$—$CR^5R^5$—$CR^5R^5$— (b-4)
—$CR^5R^5$—$CR^5R^5$—$CR^5R^5$—O— (b-5)
—O—$CR^5R^5$—$CR^5R^5$—$CR^5R^5$—O— (b-6)
—O—$CR^5R^5$—$CR^5R^5$—$CR^5R^5$—$CR^5R^5$— (b-7)
—$CR^5R^5$—$CR^5R^5$—$CR^5R^5$—$CR^5R^5$—O— (b-8) and
—O—$CR^5R^5$—$CR^5R^5$—$CR^5R^5$—O— (b-9)
wherein $R^5$ is selected from the group of hydrogen; halo; hydroxy; alkyloxy and alkyl;
$R^4$ is selected from the group of hydrogen; alkyl; arylalkyl; alkyloxyalkyl; alkylcarbonyloxyalkyl; alkyloxycarbonylalkyl; arylcarbonylalkyl; alkylsulphonyloxyalkyl; aryloxyaryl; alkyloxycarbonylaryl; alkylcarbonyl; arylalkylcarbonyl; alkyloxycarbonylalkylcarbonyl; arylcarbonyl; alkyloxycarbonyl; aryloxycarbonyl; arylalkyloxycarbonyl; mono- or di(alkyl)aminocarbonyl; mono- or di(aryl)aminocarbonyl; mono- or di(arylalkyl)aminocarbonyl; mono- or di(alkyloxycarbonylalkyl)aminocarbonyl; alkyloxyalkylaminocarbonyl; mono-, di- or tri(alkyl)amidino; mono-, di- or tri(aryl)amidino; mono-, di- or tri(arylalkyl)amidino; alkylsulphonyl; arylalkylsulphonyl or arylsulphonyl;
each $R^{10}$ is independently from each other, alkyl or cyano;
A and B are, each independently from each other, aryl or an heteroaryl radical fused to the central ring and selected from the group of furyl; thienyl; pyrrolyl; oxazolyl; thiazolyl; imidazolyl; isoxazolyl; isothiazolyl; oxadiazolyl; triazolyl; pyridinyl; pyridazinyl; pyrimidinyl; pyrazinyl; indolyl; indolizinyl; isoindolyl; benzofuryl; isobenzofuryl; benzothienyl; indazolyl; benzimidazolyl; benzthiazolyl; quinolizinyl; quinolinyl; isoquinolinyl; phthalazinyl; quinazolinyl; quinoxalinyl; chromenyl; naphthyridinyl and naphthalenyl; providing at least one of A and B is one of the above heteroaryl radicals;
each $R^9$ is, independently from each other, selected from the group of hydrogen; halo; cyano; hydroxy; carboxyl; nitro; amino; mono- or di(alkyl)amino; alkylcarbonylamino; aminosulfonyl; mono- or di(alkyl)aminosulfonyl; alkyl; alkenyl; alkyloxy; alkylcarbonyl and alkyloxycarbonyl;
Y represents O; S; S(=O); S(=O)$_2$ or $NR^8$;
X represents $C^6R^7$; O; S; S(=O); S(=O)$_2$ or $NR^8$; wherein $R^6$ and $R^7$ each independently are selected from the group of hydrogen; hydroxy; alkyl and alkyloxy; or
$R^6$ and $R^7$ taken together may form a radical selected from the group of methylene (i.e. =CH$_2$); mono- or di(cyano) methylene; a bivalent radical of Formula —(CH2)2-; —(CH2)3-; —(CH2)4-; —(CH2)5-; —O—(CH2)2-O—; —O(CH2)3O —; or, together with the carbon atom to which they are attached, a carbonyl;
$R^8$ is selected from the group of hydrogen; alkyl; alkylcarbonyl; arylcarbonyl; arylalkyl; arylalkylcarbonyl; alkylsulfonyl; arylsulfonyl and arylalkylsulfonyl;
aryl is phenyl or naphthyl, each optionally substituted with 1, 2 or 3 substituents selected from the group of halo; nitro; cyano; hydroxy; alkyloxy or alkyl;
alkyl represents a straight or branched saturated hydrocarbon radical having from 1 to 10 carbon atoms, a cyclic saturated hydrocarbon radical having from 3 to 8 carbon atoms or a saturated hydrocarbon radical containing a straight or branched moiety having from 1 to 10 carbon atoms and a cyclic moiety having from 3 to 8 carbon atoms; each radical optionally substituted with one or more halo; cyano; oxo; hydroxy; formyl; carboxyl or amino radicals;
alkenyl represents a straight or branched unsaturated hydrocarbon radical having from 1 to 6 carbon atoms or a cyclic unsaturated hydrocarbon radical having from 3 to 6 carbon atoms; said radical having one or more double bonds and said radical being optionally substituted with one or more halo cyano; oxo; hydroxy; formyl; carboxyl or amino radicals; and
halo represents fluoro; chloro; bromo and iodo.

The invention also relates to a compound according to the invention for use as a medicine.

The invention also relates to a pharmaceutical composition comprising a pharmaceutically acceptable carrier or diluent and, as active ingredient, a therapeutically effective amount of a compound according to the invention.

The invention also relates to the use of a compound according to the invention for the preparation of a medicament for the prevention and/or treatment of conditions, either prophylactic or therapeutic or both, mediated through the 5-HT$_2$, and D$_2$ receptor, as well as the through norepinephrine reuptake inhibition.

In particular, the invention relates to the use of a compound according to the invention for the preparation of a medicament for the treatment and/or prevention of central nervous system disorders like anxiety, depression and mild depression, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children, aggression, memory disorders and attitude disorders in older people, addiction, obesity, bulimia and similar disorders.

More in particular, the invention relates to the use of a compound according to the invention for the preparation of a medicament for the treatment and/or prevention of anxiety, depression, psychosis, schizophrenia, migraine and addictive properties of drugs of abuse.

DETAILED DESCRIPTION OF THE INVENTION

In a preferred embodiment, the invention relates to a compound according to the general Formula (I), the pharmaceutically acceptable acid or base addition salts thereof, the stereochemically isomeric forms thereof, the N-oxide form thereof and a prodrug thereof, wherein $R^1$ and $R^2$ each, independently from each other, are hydrogen or alkyl, each alkyl radical optionally substituted with hydroxy; or $R^1$ and $R^2$ taken together with the nitrogen atom to which they are attached, to form a radical of Formula (a-3) or (a-5), wherein m=an integer, equal to 1 or 2. Preferably, alkyl is methyl or ethyl.

In a further preferred embodiment, the invention relates to a compound according to the general Formula (I), the pharmaceutically acceptable acid or base addition salts thereof, the stereochemically isomeric forms thereof, the N-oxide form thereof and a prodrug thereof, wherein A and B, each independently from each other, is aryl or an heteroaryl radical selected from thienyl and pyridinyl, providing that at least one of A and B is an heteroaryl radical. Preferably, A is a phenyl-moiety and the thienyl moiety is a thienyl moiety wherein S is at position 9 or 11.

In a further preferred embodiment, the invention relates to a compound according to the general Formula (I), the pharmaceutically acceptable acid or base addition salts thereof, the stereochemically isomeric forms thereof, the N-oxide form thereof and a prodrug thereof, wherein X is S, A is a phenyl-moiety and B is a thienyl moiety wherein S is at position 9 or 11. Most preferably, S is at position 9.

In a further preferred embodiment, the invention relates to a compound according to the general Formula (I), the pharmaceutically acceptable acid or base addition salts thereof, the stereochemically isomeric forms thereof, the N-oxide form thereof and a prodrug thereof, wherein Y is O.

In a further preferred embodiment, the invention relates to a compound according to the general Formula (I), the pharmaceutically acceptable acid or base addition salts thereof, the stereochemically isomeric forms thereof, the N-oxide form thereof and a prodrug thereof, wherein Y is $CR^6R^7$, O, S, S(=O), S(=O)$_2$ or $NR^8$. Preferably, $CR^6R^7$ is $CH_2$. Preferably, $NR^8$ is N-benzyl.

In a further preferred embodiment, the invention relates to a compound according to the general Formula (I), the pharmaceutically acceptable acid or base addition salts thereof, the stereochemically isomeric forms thereof, the N-oxide form thereof and a prodrug thereof, wherein:
n is an integer equal to 1;
i is an integer equal to 0;
j is an integer equal to 0 or 1;
r is an integer equal to 0;
$R^1$ and $R^2$ are, each independently from each other, hydrogen, methyl, ethyl, or hydroxyethyl;
A is phenyl;
B is thienyl or pyridinyl
$R^9$ is hydrogen;
$R^{10}$ is hydrogen, hydroxymethyl, methoxycarbonyl or ethoxycarbonyl;
Y is O;
X is $CH_2$, S or N-benzyl.

In the framework of this application, alkyl is defined as a monovalent straight or branched saturated hydrocarbon radical having from 1 to 10 carbon atoms, for example methyl, ethyl, propyl, butyl, 1-methylpropyl, 1,1-dimethylethyl, pentyl, hexyl; alkyl further defines a monovalent cyclic saturated hydrocarbon radical having from 3 to 8 carbon atoms, for example cyclopropyl, methylcyclopropyl, cyclobutyl, cyclopentyl and cyclohexyl. The definition of alkyl also comprises an alkyl radical that is optionally substituted on one or more carbon atoms with one or more phenyl, halo, cyano, oxo, hydroxy, formyl and amino radicals, for example hydroxyalkyl, in particular hydroxymethyl and hydroxyethyl and polyhaloalkyl, in particular difluoromethyl and trifluoromethyl.

In the framework of this application, alkenyl is defined as an alkyl radical as defined above further comprising one or more double bonds, for example ethenyl, propenyl, butenyl, pentenyl, hexenyl, cyclopropenyl, methylcyclopropenyl, cyclobutenyl, cyclopentenyl and cyclohexenyl. The definition of alkenyl also comprises an alkenyl radical that is optionally substituted on one or more carbon atoms with one or more phenyl, halo, cyano, oxo, hydroxy, formyl and amino radicals, for example hydroxyalkenyl, in particular hydroxyethenyl.

In the framework of this application, halo is generic to fluoro, chloro, bromo and iodo.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. In particular, when hydrogen is mentioned, it is understood to refer to $^1H$, $^2H$, $^3H$ and mixtures thereof; when carbon is mentioned, it is understood to refer to $^{11}C$, $^{12}C$, $^{13}C$, $^{14}C$ and mixtures thereof; when nitrogen is mentioned, it is understood to refer to $^{13}N$, $^{14}N$, $^{15}N$ and mixtures thereof; when oxygen is mentioned, it is understood to refer to $^{14}O$, $^{15}O$, $^{16}O$, $^{17}O$, $^{18}O$ and mixtures thereof; and when fluor is mentioned, it is understood to refer to $^{18}F$, $^{19}F$ and mixtures thereof.

The compounds according to the invention therefore also comprise compounds with one or more isotopes of one or more element, and mixtures thereof, including radioactive compounds, also called radiolabelled compounds, wherein one or more non-radioactive atoms has been replaced by one of its radioactive isotopes. By the term "radiolabelled compound" is meant any compound according to Formula (I), an N-oxide form, a pharmaceutically acceptable addition salt or a stereochemically isomeric form thereof, which contains at least one radioactive atom. For example, compounds can be labelled with positron or with gamma emitting radioactive isotopes. For radioligand-binding techniques (membrane receptor assay), the $^3$H-atom or the $^{125}$I-atom is the atom of choice to be replaced. For imaging, the most commonly used positron emitting (PET) radioactive isotopes are $^{11}$C, $^{18}$F, $^{15}$O and $^{13}$N, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}$F, $^{99m}$Tc, $^{201}$Tl and $^{123}$I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and mandelic acid.

Conversely said acid addition salt forms can be converted into the free base form by treatment with an appropriate base.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate acid.

Quaternary ammonium salts of compounds according to Formula (I) defines said compounds which are able to form by a reaction between a basic nitrogen of a compound according to Formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has a positively charged nitrogen. Pharmaceutically acceptable counterions include chloro, bromo, iodo, trifluoroacetate and acetate ions.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g. of the piperazinyl or piperidinyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

The compounds according to the invention may possess at least one oxidizable nitrogen (i.e. the tertiary amines moiety in the case $R^1$ and $R^2$ are both not equal to H). In which case, it is highly likely that N-oxides are formed in the human metabolism.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. R* and S* each indicate optically pure stereogenic centers with undetermined absolute configuration. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

The compounds of Formula (I) have at least one asymmetric center at the carbon atom in the five membered ring attached to the alkylamino side chain. Said asymmetric center and any other asymmetric center which may be present (e.g. certain X groups), are indicated by the descriptors R and S.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the Formula—COOR$^x$, where R$^x$ is a C$_{1-6}$alkyl, phenyl, benzyl or one of the following groups:

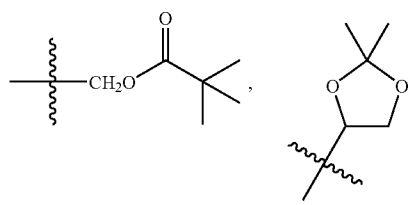

Amidated groups include groups of the Formula—CONR$^y$R$^z$, wherein R$^y$ is H, C$_{1-6}$alkyl, phenyl or benzyl and R$^z$ is —OH, H, C$_{1-6}$alkyl, phenyl or benzyl. Compounds according to the invention having an amino group may be derivatised with a ketone or an aldehyde such as formaldehyde to form a Mannich base. This base will hydrolyze with first order kinetics in aqueous solution.

Pharmacology

The compounds of the present invention, in particular compounds according to the general Formula (I), the pharmaceutically acceptable acid or base addition salts thereof, the stereochemically isomeric forms thereof, the N-oxide form thereof and a prodrug thereof, show affinity for 5-HT$_2$ receptors, particularly for 5-HT$_{2A}$ and 5-HT$_{2C}$ receptors (nomenclature as described by D. Hoyer in "Serotonin (5-HT) in neurologic and psychiatric disorders" edited by M. D. Ferrari and published in 1994 by the Boerhaave Commission of the University of Leiden) and affinity for the D$_2$ receptor as well as norepinephrine reuptake inhibition activity. The serotonin antagonistic properties of the present compounds may be demonstrated by their inhibitory effect in the "5-hydroxytryptophan Test on Rats" which is described in Drug Dev. Res., 13, 237-244 (1988).

The compounds of the present invention, in particular compounds according to the general Formula (I), the pharmaceutically acceptable acid or base addition salts thereof, the stereochemically isomeric forms thereof, the N-oxide form thereof and a prodrug thereof also have favourable physicochemical properties. For instance, they are chemically stable compounds.

In view of their capability to block 5-HT$_2$ receptors, and in particular to block 5-HT$_{2A}$ and 5-HT$_{2C}$ receptors, as well as the D$_2$ receptor and by also effecting the norepinephrine reuptake inhibition activity, the compounds of the present invention, in particular compounds according to the general Formula (I), the pharmaceutically acceptable acid or base addition salts thereof, the stereochemically isomeric forms thereof, the N-oxide form thereof and a prodrug thereof, are useful as a medicine, in particular in the prophylactic and therapeutic treatment of conditions mediated through these receptors.

The invention therefore relates to a compound according to the general Formula (I), the pharmaceutically acceptable acid or base addition salts thereof, the stereochemically isomeric forms thereof, the N-oxide form thereof and prodrugs thereof, for use as a medicine.

The invention also relates to the use of a compound according to the general Formula (I), the pharmaceutically acceptable acid or base addition salts thereof, the stereochemically isomeric forms thereof, the N-oxide form thereof and prodrugs thereof for the manufacture of a medicament for the prevention and/or treatment of conditions mediated through the 5HT$_2$ receptor, in particular 5HT$_{2A}$ and 5HT$_{2C}$ receptor and D$_2$ receptor, as well as the through norepinephrine reuptake inhibition.

In view of these pharmacological and physicochemical properties, the compounds according to the general Formula (I), the pharmaceutically acceptable acid or base addition salts thereof, the stereochemically isomeric forms thereof, the N-oxide form thereof and prodrugs thereof, are useful as therapeutic agents in the treatment and/or the prevention of central nervous system disorders like anxiety; depression and mild depression; bipolar disorders including bipolar mania and depression; sleep- and sexual disorders; psychosis; borderline psychosis; schizophrenia; migraine; personality disorders; obsessive-compulsive disorders; social phobias; panic attacks; attention disorders including attention deficit hyperactivity disorder (ADHD); organic mental disorders; mental disorders in children such as ADHD; aggression; memory disorders and attitude disorders, especially in older people; addiction; obesity; bulimia and similar disorders.

In particular, the present compounds may be used as anxiolytics, antidepressants, antipsychotics, anti-schizophrenia agents, anti-migraine agents and as agents having the potential to overrule the addictive properties of drugs of abuse.

The compounds of the present invention, in particular compounds according to the general Formula (I), the pharmaceutically acceptable acid or base addition salts thereof, the stereochemically isomeric forms thereof, the N-oxide form thereof and a prodrug thereof may also be used as therapeutic agents in the treatment of motoric disorders. It may be advantageous to use the present compounds in combination with classical therapeutic agents for such disorders.

The compounds of the present invention, in particular compounds according to the general Formula (I), the pharmaceutically acceptable acid or base addition salts thereof, the stereochemically isomeric forms thereof, the N-oxide form thereof and a prodrug thereof, may also serve in the treatment or the prevention of damage to the nervous system caused by trauma, stroke, neurodegenerative illnesses, cognitive disorders such as dementia and Alzheimers disease and the like; cardiovascular disorders like high blood pressure, thrombosis, stroke, and the like; and gastrointestinal disorders like dysfunction of the motility of the gastrointestinal system and the like.

In view of the above uses, it follows that the present invention also provides a method of treating warm-blooded animals suffering from such diseases, said method comprising the systemic administration of a therapeutic amount of a compounds of the present invention, in particular compounds according to the general Formula (I), the pharmaceutically acceptable acid or base addition salts thereof, the stereochemically isomeric forms thereof, the N-oxide form thereof and a prodrug thereof, effective in treating the above described disorders, in particular, in treating anxiety, psychosis, depression, bi-polar disorders including bipolar depression, migraine and addictive properties of drugs of abuse.

The present invention thus also relates to compounds of the present invention, in particular compounds according to the general Formula (I), the pharmaceutically acceptable acid or base addition salts thereof, the stereochemically isomeric forms thereof, the N-oxide form thereof and a prodrug thereof for use as a medicine, in particular, the compounds of Formula (I) may be used for the manufacture of a medicament for treating anxiety, psychosis, depression, bipolar disorders including bipolar depression, migraine and addictive properties of drugs of abuse.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof, the N-oxide form thereof and a prodrug thereof.

The compounds according to the invention, in particular the compounds according to Formula (I), the pharmaceutically acceptable acid or base addition salts thereof, the stereochemically isomeric forms thereof, the N-oxide form thereof and the prodrugs thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds according to the invention in pharmaceutical compositions.

Preparation

The compounds according to the invention can generally be prepared by a succession of steps, each of which is known to the skilled person.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Suitable preparation schemes for the compounds of the invention include the following:

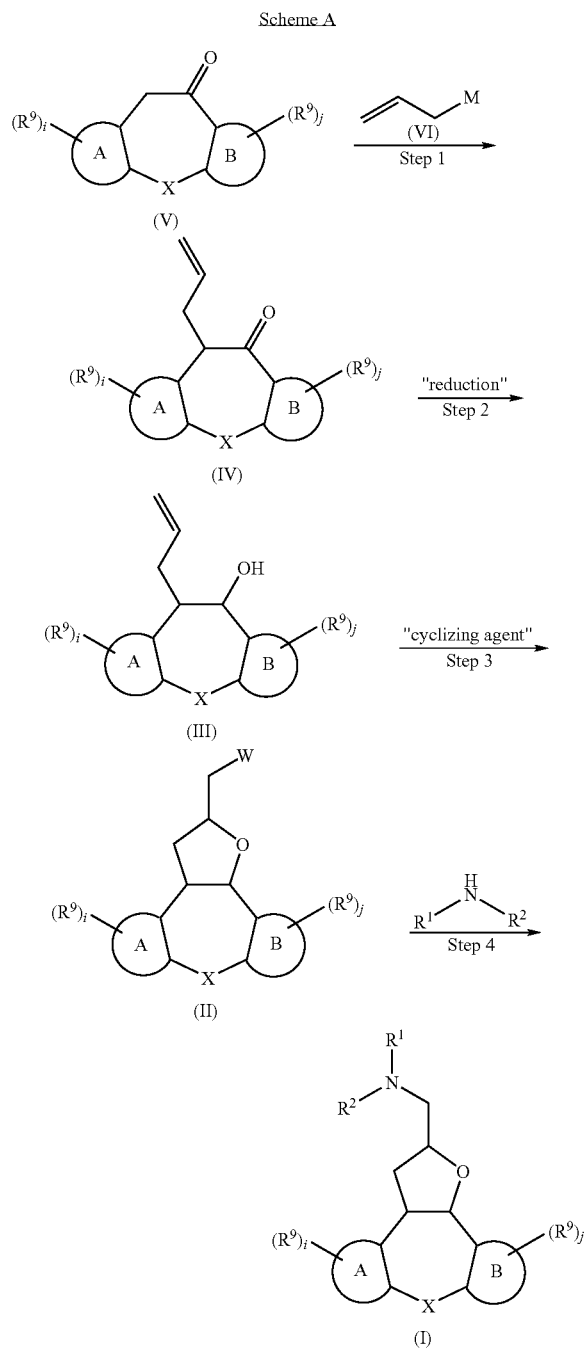

Scheme A

Step 1: Reaction of an intermediate compound according to Formula (V) with a reagent of Formula (VI). This reaction can be performed by any one of the art-known procedures for alkylation of ketones in position α under acidic or basic reaction conditions (for example the reaction can be done in an organic solvent such as tetrahydrofuran, with a base such as, for example, sodium hydride or lithium N,N-diisopropylamine and using allyl bromide as the alkylating agent) and yields an intermediate compound according to Formula (IV) wherein $R^9$, i, j, ring A, ring B and X all have the meaning as described above for a final compound according to Formula (I). For a compound according to Formula (VI), M is a suitable group for an alkylation reaction, such as, for example halo, hydroxy or acetoxy.

Step 2: Reduction of a compound according to Formula (IV) for example with sodium borohydride in an organic solvent such as tetrahydrofuran or methanol, typically at room temperature, to yield a compound according to Formula (III).

Step 3: Reaction of an intermediate compound according to Formula (III) with a cyclizing agent, such as, for example, iodine together with sodium hydrogencarbonate, in an organic solvent, such as, for example acetonitrile or dichloromethane, yields an intermediate compound according to Formula (II), which is novel, wherein W represents a suitable leaving group, preferably a halo, alkyl- or arylsulphonyloxy, in particular 4-(methylphenyl)sulphonyloxy or iodo.

Step 4: N-alkylation of an intermediate compound according to Formula (II) with an amine of Formula $HNR^1R^2$, wherein $R^1$ and $R^2$ are defined as in Formula (I), by any of the art-known procedures, yields a final compound according to Formula (I), which is novel. For instance, said N-alkylation can conveniently be carried out as described in WO 97/38991 in a reaction-inert solvent such as, for example, methanol, methylisobutyl ketone, N,N-dimethylformamide or dimethylsulfoxide, and optionally in the presence of a suitable base. Stirring and elevated temperatures, for instance reflux temperature, may enhance the rate of the reaction. Typical reaction conditions are 8 hours at 130° C.

Alternatively, said N-alkylation may also be performed using the procedure described by Monkovic et al. (J. Med. Chem. (1973), 16(4), p. 403-407) which involves the use of a pressurised reaction vessel.

Alternatively, said N-alkylation may also be performed by heating at high temperature, for example 120° C., an intermediate compound according to Formula (II), an amine of Formula $NHR^1R^2$ and a base, for example calcium oxide, in an organic solvent such as THF, in a pressurised reaction vessel.

The compounds of Formula (I) may also be converted into each other following art-known transformation reactions. For instance, a) a compound according to Formula (I), wherein $R^1$ and $R^2$ taken together with the nitrogen atom to which they are attached form a radical of Formula (b), may be converted into the corresponding primary amine by treatment with hydrazine or aqueous alkali;

b) a compound according to Formula (I), wherein $R^1$ or $R^2$ is trifluoromethylcarbonyl, may be converted into the corresponding primary or secondary amine by hydrolysis with aqueous alkali;

c) a compound according to Formula (I), wherein $R^1$ or $R^2$ is $C_{1-6}$ alkyl substituted with $C_{1-6}$ alkylcarbonyloxy may be hydrolyzed into a compound according to Formula (I) wherein $R^1$ or $R^2$ is $C_{1-6}$ alkyl substituted with hydroxy;

d) a compound according to Formula (I), wherein $R^1$ and $R^2$ are both hydrogen may be mono- or di-N-alkylated to the corresponding amine form;

e) a compound according to Formula (I), wherein $R^1$ and $R^2$ are both hydrogen, or $R^1$ or $R^2$ is hydrogen, may be N-acylated to the corresponding amide;

f) a compound according to Formula (I), containing a $C_{1-6}$alkyloxycarbonyl group may be hydrolyzed to the corresponding carboxylic acid;

g) a compound according to Formula (I) in which $R^9$ is hydrogen, i.e. i and/or j is zero, can be converted to a corresponding alkyloxycarbonyl compound by treatment with an appropriate acylating agent, e.g. the appropriate alkyloxycarbonyl chloride in the presence of butyllithium in hexane using an organic solvent such as tetrahydrofuran; or h) a compound according to Formula (I) in which $R^9$ is alkyloxycarbonyl can be converted to a corresponding hydroxymethyl compound by reduction for example with LiAlH$_4$ for example in an organic solvent such as tetrahydrofuran.

The intermediate compounds mentioned hereinabove are either commercially available or may be made following art-known procedures. For instance, intermediate compounds of Formula (II) may be prepared according to the procedure described by Monkovic et al. (J. Med. Chem. (1973), 16(4), p. 403-407).

The intermediate compounds of Formula (V) in which X is CH$_2$, A is a phenyl group and B is a thienyl group, represented by Formula (V-a) below, are commercially available or may be made following art-known procedures. For instance, intermediate compounds of Formula (V-a) may be prepared according to the procedure described by Protiva et al. (Collection of Czechoslovak Chemical Communications 1969, 34(2), 468-478).

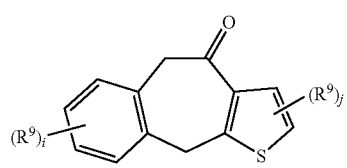

(V-a)

The intermediate compounds of Formula (V) in which X is S, A is a phenyl group and B is a thienyl group, represented by Formula (V-b) below, may be prepared by reduction of an intermediate compound according to Formula (VI) with a suitable reducing agent, such as aluminium hydride, in an organic solvent such as, for example, tetrahydrofuran.

Scheme B

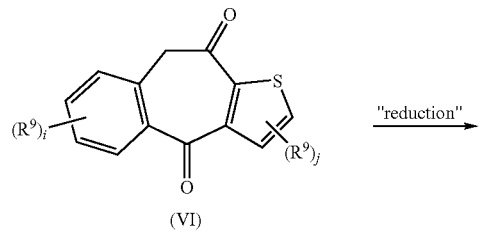

(VI)

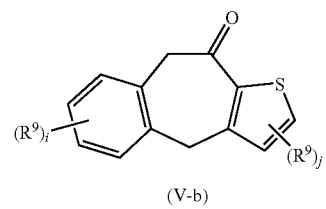

(V-b)

An intermediate compound according to Formula (VI) may be prepared by the procedures described by Michal Majchrzak (Journal of Heterocyclic Chemistry 1985, 22 (5), 1203-4; Journal of Heterocyclic Chemistry 1985, 22(5), 1205-6) and in patent publications DE2625642 and PL158223. The intermediate compounds of Formula (V) in which X is S, A is a phenyl group and B is a thienyl group, represented by Formula (V-c) below, are commercially available or may be made following art-known procedures. For instance, intermediate compounds of Formula (V-c) may be prepared according to the procedures described in patent publications CS142473, CS217949 and/or CS200271.

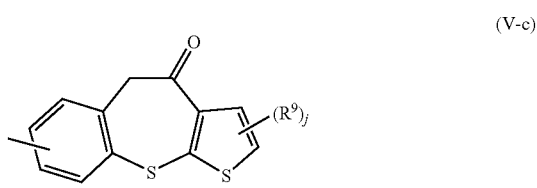

(V-c)

The intermediate compounds of Formula (V) in which X is NR$^8$, A is a phenyl group and B is a pyridinyl group, represented by Formula (V-d) below, may be prepared according to the reaction sequence shown in Scheme C.

Scheme C

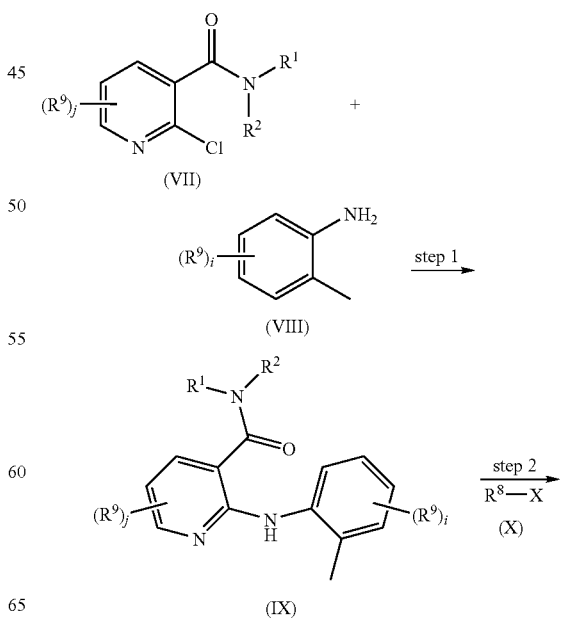

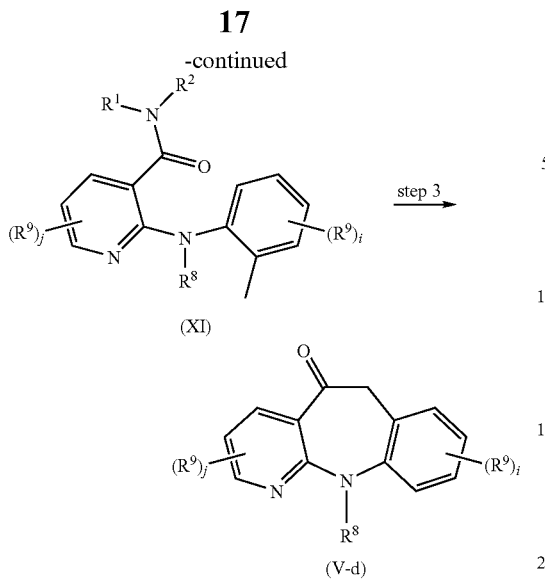

(XI)

(V-d)

Step 1: Reaction of a compound according to Formula (VII) with a compound according to Formula (VIII) at high temperature, such as for example 200° C. to give an intermediate compound according to Formula (IX) wherein $R^1$, $R^2$, $R^9$, i, j, have the meanings as described above for the final compound according to Formula (I).

Step 2: Reaction of a compound according to Formula (IX) with a compound according to Formula (X) in the presence of a base, such as for example sodium hydride, in an organic solvent such as for example N,N-dimethylformamide. Alternatively, the reaction can be carried out by any of the art-known procedures for the alkylation of aniline derivatives. For a compound according to Formula (X), X is a suitable group for an alkylation reaction, such as, for example halo, hydroxy or acetoxy and $R^8$ has the meaning as described above for the final compound according to Formula (I).

Step 3: Cyclization of an intermediate compound according to Formula (XI) gives a compound according to Formula (V-d) wherein $R^8$, $R^9$, i, j, have the meanings as described above for the final compound according to Formula (I). The cyclization reaction can be effected by art-known procedures, such as the procedure described by Lohse et al. (Tetrahedron Letters, 2001, 42, 385-389).

Pure stereochemically isomeric forms of the compounds of Formula (I) may be obtained by the application of art-known procedures. Diastereomers may be separated by physical methods such as selective crystallization and chromatographic techniques, e.g. counter-current distribution, liquid chromatography and the like.

The compounds of Formula (I) as prepared in the hereinabove described processes are generally racemic mixtures of enantiomers which can be separated from one another following art-known resolution procedures. The racemic compounds of Formula (I) which are sufficiently basic or acidic may be converted into the corresponding diastereomeric salt forms by reaction with a suitable chiral acid respectively with a suitable chiral base. Said diastereomeric salt forms are subsequently separated, for example, by selective or fractional crystallization and the enantiomers are liberated therefrom by alkali or acid. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The following examples are intended to illustrate and not to limit the scope of the present invention.

EXPERIMENTAL PART

Hereinafter, "DCM" is defined as dichloromethane; "THF" is defined as tetrahydrofuran; "BuLi" is defined as n-butyl-lithium; "EtOAc" is defined as ethyl acetate; and "MeOH" is defined as methanol.

A. Preparation of the Intermediate Compounds

Example A1 a) Preparation of Intermediate Compound 1

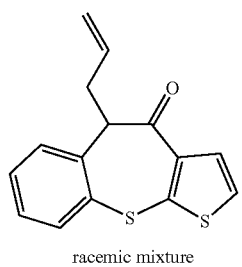

racemic mixture

Reaction under $N_2$ atmosphere: a solution of thieno[2,3-b][1]benzothiepin-4(5H)-one (0.03998 mol) in THF dry (750 ml) was cooled to 0° C. and then sodium hydride 60% in mineral oil (0.040 mol) was added portionwise. The reaction mixture was stirred for 45 min. at 0° C., then at room temperature for 1 hour. After cooling to 0° C., a mixture of 3-bromo-1-propene (0.40 mol) in THF dry (250 ml) was added dropwise and the resulting mixture allowed to reach room temperature overnight. Water was added and the organic solvent was evaporated. The aqueous concentrate was extracted two times with DCM; the organic layers were combined, dried ($Na_2SO_4$) and the solvent was evaporated (vac.), yielding 10.22 g of intermediate compound 1.

b) Preparation of Intermediate Compound 2

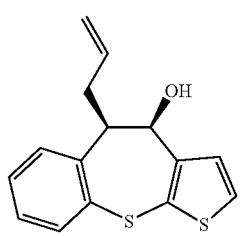

racemic mixture of cis/trans diastereoisomers 90/10

A solution of intermediate compound 1 (0.03744 mol) in THF (200 ml) was cooled to 0° C. and sodium tetrahydroborate (0.045 mol) was added portionwise. After 10 min., MeOH (100 ml) was added dropwise, the reaction mixture was warmed to room temperature and stirred further overnight. The mixture was quenched with a saturated aqueous saturated aqueous ammonium chloride solution. and the organic solvent was evaporated (vac.). The aqueous concentrate was extracted two times with DCM; the organic layers were combined, washed with brine and with water, then dried (Na$_2$SO$_4$). The solvent was evaporated (vac.) and the residue was purified by short open column chromatography. The product fractions were collected and the solvent was evaporated, yielding (mixture of isomers: cis/trans 90/10) intermediate compound 2.

c) Preparation of Intermediate Compound 3

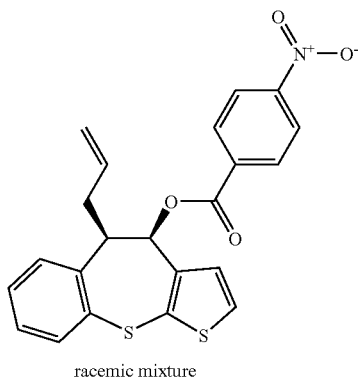

racemic mixture

A solution of triphenyl-phosphine (0.073 mol) in THF (q.s.) was stirred under N$_2$ at 0° C., bis(1-methylethyl) diazenedicarboxylate (0.071 mol) was added and the resulting suspension was stirred for 0.5 hour. A solution of intermediate compound 2 (0.036 mol) and 4-nitro-benzoic acid (0.073 mol) in THF (q.s.) was added dropwise, the reaction mixture was gradually warmed to room temperature and stirred for 16 hours. The solvent was evaporated and the residue was dissolved in DCM, washed with water and with brine, then dried (Na$_2$SO$_4$). The solvent was evaporated and the residue was purified by preparative high-performance liquid chromatography (eluent: EtOAc/Heptane 2/8). The pure fractions were collected and the solvents was evaporated, yielding intermediate compound 3.

d) Preparation of Intermediate Compound 4

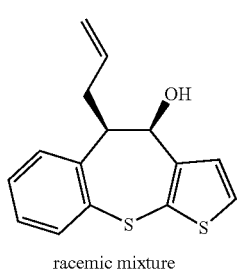

racemic mixture

A mixture of intermediate compound 3 (0.018 mol) was stirred in THF (200 ml) at 0° C. and then a mixture of lithium hydroxide (0.020 mol) in water (50 ml) was added dropwise. The reaction mixture was allowed to reach room temperature for 16 hours and the organic solvent was evaporated. The aqueous concentrate was washed with DCM; the organic layer was separated, dried (Na$_2$SO$_4$) and the solvent was evaporated under reduced pressure, yielding 5.43 g of intermediate compound 4.

e) Preparation of Intermediate Compounds 5 and 6

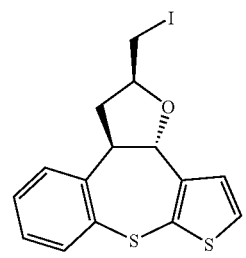

and intermediate compound 5
[2RS-(2β, 3aα, 11bβ)]

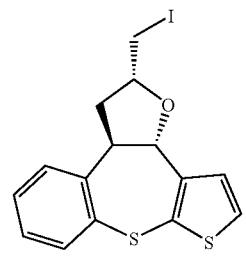

intermediate compound 6
[2RS-(2α, 3aα, 11bβ)]

Bis(pyridine)iodinium tetrafluoroborate (0.0186 mol) was added portionwise to a mixture of intermediate compound 4 (0.0169 mol) in DCM (q.s.) at room temperature under N$_2$ atmosphere and the resulting solution was stirred for 1 hour, then a sodium thiosulfate aqueous solution was added. The organic layer was separated, dried (Na$_2$SO$_4$) and the solvent was evaporated under reduced pressure. The residue was purified by preparative. high-performance liquid chromatography. Two product fractions were collected and the solvents were evaporated, yielding 2.5 g of intermediate compound 5 and 2.1 g of intermediate compound 6.

B. Preparation of the Final Compounds

Example B1

Preparation of Final Compound 1 (free base) and 2

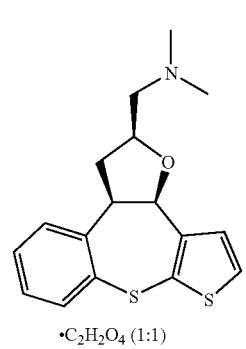

·C$_2$H$_2$O$_4$ (1:1)

A mixture of intermediate compound 5 (0.00127 mol), dimethylamine (0.020 mol, 2M in THF) and calcium oxide (0.100 g) in THF (10 ml) was heated at 120° C. (oil bath temperature) into a Parr reactor vessel for 8 hours and then the reaction mixture was cooled to room temperature. The solids were filtered off and the organic solvent was evaporated. The residue thus obtained was purified in a manifold (vac.) using a Sep-Pak silica cartridge (eluent: DCM/(MeOH/NH$_3$) mixtures). The product fractions were collected and the solvent was evaporated to yield compound 1, namely the free base of compound 2. The residue was converted into the ethanedioic acid salt by treatment with ethanedioic acid in diethyl ether. The resulting precipitate was filtered off, washed with cold diethylether and dried, yielding final compound 2 (mixture of diastereoisomers 80/20).

Example B2

Preparation of Compound 3

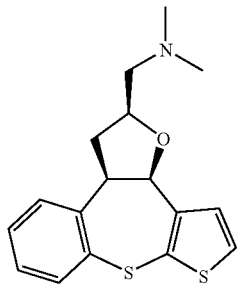

A mixture of intermediate compound 6 (0.00145 mol), dimethylamine 2M in THF (0.020 mol) and calcium oxide (0.200 g) in THF (20 ml) was heated in a Parr reactor vessel for 10 hours at 120° C. (oil bath temperature), then the reaction mixture was cooled to room temperature and the solids were filtered off. The organic solvent was evaporated and the residue thus obtained was taken up in DCM and washed with a saturated aqueous NaHCO$_3$ solution. The organic layer was separated, dried (Na$_2$SO$_4$), filtered off and the solvent was evaporated. The residual oil was purified in a manifold (vac.) using a Sep-Pak silica cartridge (eluent: DCM/(MeOH/NH$_3$)). The product fractions were collected and the solvent was evaporated, yielding final compound 3.

Example B3

Preparation of Final Compound 4

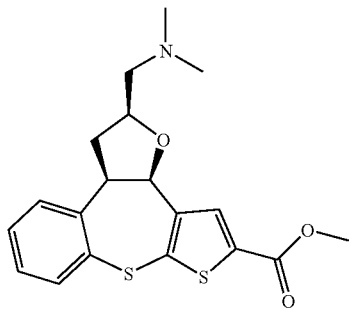

Reaction under N$_2$ atmosphere: a solution of final compound 3 (0.00104 mol) in THF dry (15 ml) was cooled to −78° C. and then BuLi 1.6M in hexane (0.0011 mol) was added dropwise. The reaction mixture was stirred at −78° C. for 35 min. and dimethyl carbonate (0.003 mol) was added. The resulting mixture was allowed to reach room temperature in 1 hour, water was added and the organic layer was evaporated. The residue thus obtained was taken up in DCM and washed with a saturated aqueous NaHCO$_3$ solution. The organic layer was separated, dried (Na$_2$SO$_4$), filtered off and the solvent was evaporated. The resulting residue was purified in a manifold (vac.) using a Sep-Pak silica cartridge. The product fractions were collected and the solvent was evaporated. The residue was further purified by high-performance liquid chromatography. The product fractions were collected and the solvent was evaporated, yielding final compound 4.

Example B4

Preparation of Final Compound 5

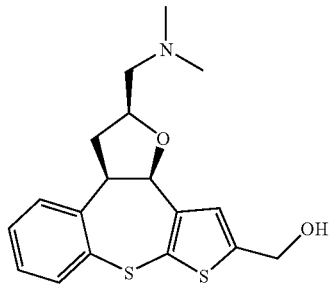

A mixture of final compound 4 (0.0004 mol) in THF (q.s.) was stirred at room temperature under N$_2$ and lithium tetrahydroaluminate (0.00044 mol) was added, then the reaction mixture was stirred for 2 hours and an aqueous saturated ammonium chloride solution was added. The organic layer was separated, dried (MgSO$_4$), filtered off and the solvent was evaporated. The residue was purified by short open column chromatography over silica gel (eluent: DCM/MeOH 97/3). The product fractions were collected and the solvent was evaporated, yield 0.153 g of final compound 5.

TABLE 1

$$\text{[Structure: tricyclic system with CH}_2\text{-NR}^1\text{R}^2 \text{ substituent, benzene ring fused to X-containing ring fused to thiophene with R}^9\text{]}$$

| Co. No. | Ex. No. | —NR¹R² | R⁹ | X | Physical data |
|---|---|---|---|---|---|
| 6 | B1 | —NHCH₃ | —H | —CH₂— | mixture of four diastereoisomers not assigned; oxalate (1:1) |
| 7 | B1 | —NHCH₃ | —H | —CH₂— | mixture (83:6:6:5) of four diastereoisomers (83) [2RS-(2α, 3aβ, 11bα)]; other diastereoisomers not assigned; oxalate (1:1) |
| 8 | B1 | —NHCH₃ | —H | —CH₂— | mixture (62:25:10:3) of four diastereoisomers (62) [2RS-(2β, 3aβ, 11bα)]; (25) [2RS-(2α, 3aα, 11bα)]; (10) [2RS-(2α, 3aβ, 11bα)]; (3) [2RS-(2β, 3aα, 11bα)]; oxalate (1:1) |
| 33 | B1 | —N(CH₃)₂ | —H | —CH₂— | mixture (95.5:4.5) of two trans fused diastereoisomers (95.5) [2RS-(2α, 3aβ, 11bα)]: (4.5) [2RS-(2β, 3aβ 11bα)]; oxalate (1:1); m.p. = 228.4° C. |
| 20 | B1 | —NHCH₃ | —H | —S— | [2RS-(2α, 3aα, 11bβ)]; oxalate (1:1) |
| 21 | B1 | —NHCH₃ | —H | —S— | [2RS-(2β, 3aα, 11bβ)] oxalate (1:1) |
| 22 | B1 | —NHCH₃ | —H | —S— | [2RS-(2β, 3aα, 11bβ)] |
| 31 | B1 | —NHCH₃ | —H | —S— | [2S*-(2β, 3aβ, 11bα)] oxalate (1:1) |
| 32 | B1 | —NHCH₃ | —H | —S— | [2RS-(2α, 3aα, 11bβ)] oxalate (1:1) |
| 9 | B1 | —N(CH₃)₂ | —H | —S— | mixture of three racemic diastereoisomers: 63% [2RS-(2α, 3aβ, 12bα)]; 28% [2RS-(2α, 3aβ, 12bβ)]; 9% not assigned; oxalate (1:1) |
| 14 | B1 | —N(CH₃)₂ | —H | —S— | [2RS-(2α, 3aα, 11bα)] oxalate (1:1) |
| 19 | B2 | —N(CH₃)₂ | —H | —S— | [2RS-(2α, 3aα, 11bβ)] oxalate (1:1) |
| 1 | B1 | —N(CH₃)₂ | —H | —S— | [2RS-(2β, 3aα, 11bβ)] |
| 2 | B1 | —N(CH₃)₂ | —H | —S— | [2RS-(2β, 3aα, 11bβ)]; oxalate (1:1); m.p. = 215.4° C. |
| 3 | B2 | —N(CH₃)₂ | —H | —S— | [2RS-(2α, 3aα, 11bβ)] |
| 10 | B1 | —N(CH₃)(CH₂CH₂OH) | —H | —S— | [2RS-(2α, 3aβ, 11bα)] oxalate (1:1); m.p. = 84.8° C. |
| 18 | B1 | —N(CH₃)(CH₂CH₂OH) | —H | —S— | [2RS-(2α, 3aα, 11bβ)] oxalate (1:1) |
| 25 | B1 | —N(CH₃)(CH₂CH₂OH) | —H | —S— | mixture (75:25) of two trans fused diastereoisomers (75) [2RS-(2α, 3aβ, 11bα)]: (25) [2RS-(2β, 3aβ, 11bα)] |
| 26 | B1 | —N(CH₃)(CH₂CH₂OH) | —H | —S— | mixture (75:25) of two trans fused diastereoisomers (75) [2RS-(2α, 3aβ, 11bα)]: (25) [2RS-(2β, 3aβ, 11bα)] |
| 11 | B1 | N-methyl-4-(2-hydroxyethyl)piperidinyl | —H | —S— | mixture of two diastereoisomers; major component: [2RS-(2α, 3aβ, 11bα)]; oxalate (1:1); m.p. = 131.2° C. |
| 13 | B1 | N-methyl-1,4-dioxa-8-azaspiro[4.5]decan-8-yl | —H | —S— | [2RS-(2α, 3aβ, 11bα)]; oxalate (1:1); m.p. = 131.7° C. |
| 17 | B1 | N-methyl-1,4-dioxa-8-azaspiro[4.5]decan-8-yl | —H | —S— | [2RS-(2α, 3aα, 11bβ)] oxalate (1:1) |
| 16 | B1 | N-methyl-3-hydroxypyrrolidinyl | —H | —S— | {2RS-[2α(3'RS), 3aα, 11bβ]} oxalate (1:1) |

TABLE 1-continued
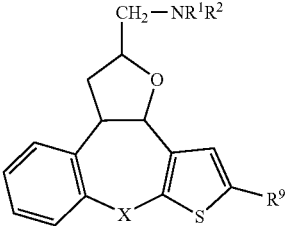
| Co. No. | Ex. No. | —NR¹R² | R⁹ | X | Physical data |
|---|---|---|---|---|---|
| 23 | B1 | 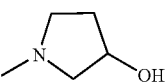 | —H | —S— | {2RS-[2β(3'RS), 3aα, 11bβ]} oxalate (1:1) |
| 24 | B1 | 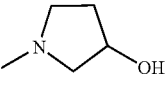 | —H | —S— | {2RS-[2β(3'RS), 3aα, 11bβ]} |
| 27 | B1 | 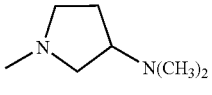 | —H | —S— | {2RS-[2α(3'RS), 3aα, 11bβ]} oxalate (1:1) |
| 28 | B1 | 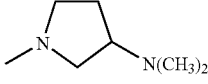 | —H | —S— | {2RS-[2α(3'RS), 3aα, 11bβ]} |
| 29 | B1 | 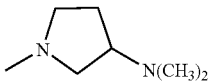 | —H | —S— | {2RS-[2β(3'RS), 3aα, 11bβ]} oxalate (1:1) |
| 30 | B1 | 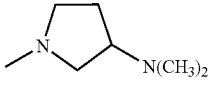 | —H | —S— | {2RS-[2β(3'RS), 3aα, 11bβ]} |
| 12 | B1 | 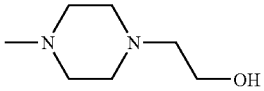 | —H | —S— | [2RS-(2α, 3aβ, 11bα)]; oxalate (1:1); m.p. = 224.6° C. |
| 15 | B1 | 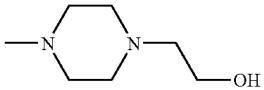 | —H | —S— | [2RS-(2α, 3aα, 11bβ)] oxalate (1:1) |
| 34 | B1 | —N(CH₃)₂ | —COOCH₂CH₃ | —S— | [2RS-(2β, 3aα, 11bα)] oxalate (1:1); m.p. = 188.9° C. |
| 4 | B3 | —N(CH₃)₂ | —COOCH₃ | —S— | [2RS-(2α, 3aα, 11bβ)] |
| 5 | B4 | —N(CH₃)₂ | —CH₂OH | —S— | [2RS-(2α, 3aα, 11bβ)] |

TABLE 2

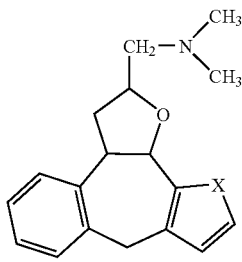

| Co. No. | Ex. No. | X | Physical data |
|---|---|---|---|
| 35 | B1 | —S— | mixture (80:15:5) of three diastereoisomers: (80) [2RS-(2α, 3aβ, 11bα)]; other diastereoisomers not assigned; oxalate (1:1) |

TABLE 3

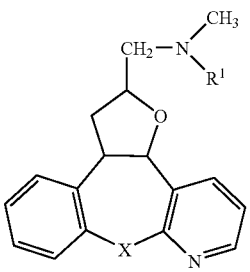

| Co. No. | Ex. No. | R$^1$ | X | Physical data |
|---|---|---|---|---|
| 36 | B1 | —H | >N(benzyl)- | mixture (60:28:6:6) of four diastereoisomers: (60:28) [2RS-(3aβ, 11bα)], stereochemistry at position two not assigned; (6:6) [2RS-3aα, 11bα)], stereochemistry at position two not assigned |
| 37 | B1 | —H | >N(benzyl)- | mixture of two trans fused diastereoisomers, stereochemistry at position 2 not assigned |

The LCMS data shown in Table 4 have been obtained by the following method:

The HPLC gradient was supplied by a HP 1100 from Agilent with a column heater set at 40° C. Flow from the column was passed through photodiode array (PDA) detector and then split to a Light Scattering detector (ELSD) and to a Waters-Micromass Time of Flight (ToF) mass spectrometer with an electrospray ionization source operated simultaneously in positive and negative ionization mode.

Reversed phase HPLC was carried out on a XDB-C18 cartridge (3.5 μm, 4.6×30 mm) from Agilent, with a flow rate of 1 ml/min. Three mobile phases (mobile phase A: 0.5 g/l ammoniumacetate solution, mobile phase B: acetonitrile; mobile phase C: methanol) were employed to run a gradient condition from 80% A, 10% B, 10% C to 50% B and 50% C in 6.0 min., to 100% B at 6.5 min., kept till 7.0 min and reequilibrated with 80% A, 10% B and 10% C at 7.6 min. that was kept till 9.0 min. An injection volume of 5 μL was used.

High Resolution Mass spectra were acquired by scanning from 100 to 750 in 1 s using a dwell time of 1 s. The capillary needle voltage was 3 kV and the source temperature was maintained at 140° C. Nitrogen was used as the nebulizer gas. Cone voltage was 30 V for both positive and negative ionization mode. Leucine-enkephaline was the reference used for the lock spray. Data acquisition was performed with a Waters-Micromass MassLynx-Openlynx data system. All parent peak masses correspond to the free base+H+.

TABLE 4

| Co. No. | Retention time | Parent peak mass (ES+) | Mw calculated |
|---|---|---|---|
| 14 | 4.17 | 318 | 317 |
| 15 | 4.53 | 403 | 402 |
| 16 | 4.20/4.25 | 360 | 359 |
| 17 | 5.7 | 416 | 415 |
| 18 | 4.48 | 348 | 347 |
| 19 | 4.32 | 318 | 317 |
| 20 | 3.52 | 304 | 303 |
| 2 | 4.46 | 318 | 317 |
| 21 | 3.74 | 304 | 303 |
| 34 | 4.91 | 390 | 389 |
| 23 | 4.22/4.41 | 360 | 359 |
| 27 | 4.65 | 387 | 386 |
| 29 | 4.64 | 387 | 386 |
| 31 | 3.64 | 304 | 303 |
| 32 | 3.63 | 304 | 303 |
| 36 | 3.40/3.63/3.93/4.01 | 372 | 371 |
| 5 | 3.63 | 348 | 347 |

C. Pharmacological Examples

Example C.1

In Vitro Binding Affinity for 5-HT$_{2A}$ and 5-HT$_{2C}$ Receptors

The interaction of the compounds of Formula (I) with 5-HT$_{2A}$ and 5-HT$_{2C}$ receptors was assessed in in vitro radioligand binding experiments. In general, a low concentration of a radioligand with a high binding affinity for the receptor is incubated with a sample of a tissue preparation enriched in a particular receptor (1 to 5 mg tissue) in a buffered medium (0.2 to 5 ml). During the incubation, the radioligands bind to the receptor. When equilibrium of binding is reached, the receptor bound radioactivity is separated from the non-bound radioactivity, and the receptor bound activity is counted. The interaction of the test compounds with the receptors is assessed in competition binding experiments. Various concentrations of the test compound are added to the incubation mixture containing the tissue preparation and the radioligand. Binding of the radioligand will be inhibited by the test compound in proportion to its binding affinity and its concentration. The radioligand used for 5-HT$_{2A}$ binding affinity is $^3$H-ketanserin and the tissue used is the frontal cortex of the rat. The radioligand used for 5-HT$_{2C}$ binding affinity is $^3$H-mesulergine and the tissue used is the choroid plexus of the pig.

Example C.2

In Vitro Determination of NET Reuptake Inhibition

Cortex from rat brain was collected and homogenised using an Ultra-Turrax T25 and a Dual homogeniser in ice-cold homogenising buffer containing Tris, NaCl and KCl (50 mM, 120 mM and 5 mM, respectively, pH 7.4) prior to dilution to an appropriate protein concentration optimised for specific and non-specific binding. Binding was performed with radioligand [$^3$H]Nixosetine (NEN, NET-1084, specific activity ~70 Ci/mmol) diluted in ice cold assay buffer containing Tris, NaCl and KCl (50 mM, 300 mM and 5 mM, respectively, pH 7.4) at a concentration of 20 nmol/L. Prepared radioligand (50 µl) was then incubated (60 min, 25° C.) with membrane preparations pre-diluted to an appropriate protein concentration (400 µl), and with 50 µl of either the 10% DMSO control, Mazindol ($10^{-6}$ mol/L final concentration), or compound of interest. Membrane-bound activity was detected by filtration through a Packard Filtermate harvester onto GF/B Unifilterplates, washed with ice-cold Tris-HCl buffer, containing NaCl and KCl (50 mM, 120 mM and 4 mM; pH 7.4; 6×0.5 ml). Filters were allowed to dry for 24 h before adding scintillation fluid. Scintillation fluid was allowed to saturate filters for 24 h before counting in a Topcount scintillation counter. Percentage specific bound and competition binding curves were calculated using S-Plus software (Insightful).

Example C.3

In Vitro Binding Affinity for Human $D_{2L}$ Receptor

Frozen membranes of human Dopamine $D_{2L}$ receptor-transfected CHO cells were thawed, briefly homogenised using an Ultra-Turrax T25 homogeniser and diluted in Tris-HCl assay buffer containing NaCl, $CaCl_2$, $MgCl_2$, KCl (50, 120, 2, 1, and 5 mM respectively, adjusted to pH 7.7 with HCl) to an appropriate protein concentration optimised for specific and non-specific binding. Radioligand [$^3$H]Spiperone (NEN, specific activity ~70 Ci/mmol) was diluted in assay buffer at a concentration of 2 nmol/L. Prepared radioligand (50 µl), along with 50 µl of either the 10% DMSO control, Butaclamol ($10^{-6}$ mol/l final concentration), or compound of interest, was then incubated (30 min, 37° C.) with 400 µl of the prepared membrane solution. Membrane-bound activity was filtered through a Packard Filtermate harvester onto GF/B Unifilterplates and washed with ice-cold Tris-HCl buffer (50 mM; pH 7.7; 6×0.5 ml). Filters were allowed to dry before adding scintillation fluid and counting in a Topcount scintillation counter. Percentage specific bound and competition binding curves were calculated using S-Plus software (Insightful).

Results

The results from the above assays are given in the following table as ($pIC_{50}$) values: "n.d." meant "not determined".

TABLE 5

| Co. No. | 5-HT$_{2A}$ | 5-HT$_{2C}$ | D$_2$ | NET-inhibition |
|---|---|---|---|---|
| 11 | 8.5 | 7.4 | 8.2 | 5.1 |
| 13 | 8.3 | 7.0 | 7.7 | <5 |
| 12 | 7.9 | 6.6 | 7.5 | <5 |
| 16 | 7.7 | 7.8 | 6.8 | 5.5 |
| 17 | 7.4 | 7.0 | 6.8 | <5 |
| 5 | n.d. | 7.7 | 6.7 | 6.4 |
| 25 | 8.0 | 8.0 | 6.7 | 6.9 |
| 10 | 7.9 | 7.7 | 6.7 | 6.7 |
| 2 | >8 | 8.1 | 6.7 | 7.2 |
| 15 | 6.7 | 6.6 | 6.6 | 5.6 |
| 23 | >8 | 8.4 | 6.6 | 5.5 |
| 27 | n.d. | 7.3 | 6.4 | <5 |
| 9 | 7.8 | 7.6 | 6.4 | 6.5 |
| 21 | >8 | 8.4 | 6.3 | 6.9 |
| 29 | n.d. | 6.6 | 6.1 | <5 |
| 35 | 8.2 | 7.8 | 6.1 | 6.3 |
| 33 | 7.0 | 7.3 | 6.1 | 6.0 |
| 18 | 7.4 | 7.4 | 6.0 | 7.5 |
| 20 | 7.1 | 7.3 | 5.9 | 7.2 |
| 19 | 7.0 | 7.6 | 5.9 | 7.5 |
| 31 | n.d. | 7.56 | 5.9 | 6.0 |

TABLE 5-continued

| Co. No. | 5-HT$_{2A}$ | 5-HT$_{2C}$ | D$_2$ | NET-inhibition |
|---|---|---|---|---|
| 37 | n.d. | 7.0 | 5.8 | 5.9 |
| 32 | n.d. | 7.3 | 5.7 | 7.4 |
| 6 | 7.4 | 7.4 | 5.6 | 5.7 |
| 7 | 6.6 | 7.7 | 5.5 | 5.6 |
| 8 | <5 | 7.2 | 5.5 | 6.0 |
| 4 | n.d. | 6.8 | 5.4 | 6.2 |
| 34 | 6.8 | 6.5 | 5.4 | 5.6 |
| 36 | n.d. | 6.2 | 5.2 | 5.3 |
| 14 | 7.1 | 6.6 | <6 | 6.3 |

D. Composition Examples

"Active ingredient" (A.I.) as used throughout these examples relates to a compound according to Formula (I), a pharmaceutically acceptable acid addition salt, a stereochemically isomeric form thereof or a N-oxide form thereof.

Example D.1

Oral Solution

Methyl 4-hydroxybenzoate (9 g) and propyl 4-hydroxybenzoate (1 g) were dissolved in boiling purified water (4 l). In 3 l of this solution were dissolved first 2,3-dihydroxybutanedioic acid (10 g) and thereafter A.I (20 g). The latter solution was combined with the remaining part of the former solution and 1,2,3-propanetriol (12 l) and sorbitol 70% solution (3 l) were added thereto. Sodium saccharin (40 g) were dissolved in water (500 ml) and raspberry (2 ml) and gooseberry essence (2 ml) were added. The latter solution was combined with the former, water was added q.s. to a volume of 20 l providing an oral solution comprising 5 mg of the active ingredient per teaspoonful (5 ml). The resulting solution was filled in suitable containers.

Example D.2

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in water (200 ml). The wet powder mixture was sieved, dried and sieved again. Then there was added microcrystalline cellulose (100 g) and hydrogenated vegetable oil (15 g). The whole was mixed well and compressed into tablets, giving 10.000 tablets, each containing 10 mg of the active ingredient.

Coating

To a solution of methyl cellulose (10 g) in denaturated ethanol (75 ml) there was added a solution of ethyl cellulose (5 g) in dichloromethane (150 ml). Then there were added dichloromethane (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinylpyrrolidone (5 g) and concentrated colour suspension (30 ml) and the whole was homogenated. The tablet cores were coated with the thus obtained mixture in a coating apparatus.

Example D.3

Injectable Solution

Methyl 4-hydroxybenzoate (1.8 g) and propyl 4-hydroxybenzoate (0.2 g) were dissolved in boiling water (500 ml) for injection. After cooling to about 50° C. there were added while stirring lactic acid (4 g), propylene glycol (0.05 g) and A.I. (4 g). The solution was cooled to room temperature and supplemented with water for injection q.s. ad 1000 ml, giving a solution comprising 4 mg/ml of A.I. The solution was sterilized by filtration and filled in sterile containers.

The invention claimed is:

1. Compound according to Formula (I)

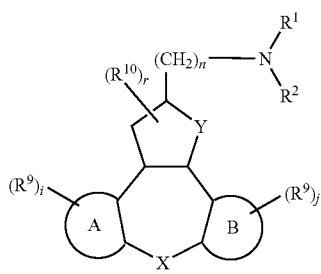

(I)

an N-oxide form, a pharmaceutically acceptable addition salt or a stereochemically isomeric form thereof, wherein:

n is an integer, equal to zero; 1; 2; 3; 4; 5 or 6;

i,j are integers, independently from each other, equal to zero; 1; 2; 3 or 4;

r is an integer, equal to zero; 1; 2; 3 or 4;

$R^1$ and $R^2$ each independently from each other, and are selected from the group consisting of hydrogen; alkylcarbonyl; alkyl; alkyloxyalkyl; alkylcarbonyloxyalkyl; alkyloxycarbonylalkyl; arylalkyl; arylcarbonyl; alkyloxycarbonyl; aryloxycarbonyl; arylalkylcarbonyl; alkyloxy-carbonylalkylcarbonyl; mono- or di(alkyl)aminocarbonyl; mono- or di(aryl)aminocarbonyl; mono- or di(arylalkyl)aminocarbonyl; mono- or di(alkyloxycarbonylalkyl)aminocarbonyl; alkylsulphonyl; arylsulphonyl; arylalkylsulphonyl; mono- or di(alkyl)aminothiocarbonyl; mono- or di(aryl)aminothiocarbonyl; mono-or di(arylalkyl)aminothiocarbonyl; mono-, di- or tri(alkyl)amidino; mono-, di- or tri(aryl)amidino and mono-, di- or tri(arylalkyl)amidino; or $R^1$ and $R^2$ taken together with the nitrogen atom to which they are attached may form a radical of a Formula selected from the group consisting of:

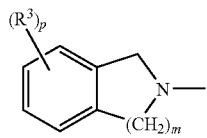

(a-1)

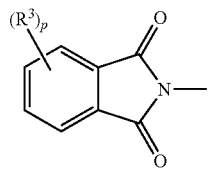

(a-2)

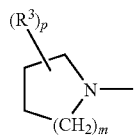

(a-3)

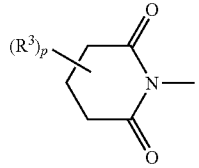

(a-4)

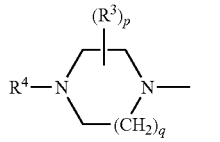

(a-5)

and

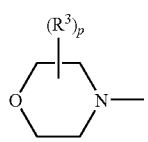

(a-6)

wherein:

p is an integer equal to zero; 1; 2; 3 or 4;

q is an integer equal to 1 or 2;

m is an integer equal to zero; 1; 2 or 3;

each $R^3$ independently from each other, is selected from the group consisting of halo; hydroxy; cyano; alkyl; alkyloxyalkyl; aryloxyalkyl; mono- or di(alkyl)aminoalkyl; hydroxycarbonylalkyl; alkyloxycarbonylalkyl; mono- or di(alkyl)aminocarbonylalkyl; mono- or di(aryl)-aminocarbonylalkyl; mono- or di(alkyl)aminocarbonyloxyalkyl; alkyloxycarbonyloxyalkyl; arylaminocarbonyloxyalkyl; arylalkylaminocarbonyloxyalkyl; aryl; alkyloxy; aryloxy; alkylcarbonyloxy; arylcarbonyloxy; arylalkylcarbonyloxy; alkylcarbonyl; arylcarbonyl; aryloxycarbonyl; hydroxycarbonyl; alkyloxycarbonyl; mono- or di-alkylamino; alkylcarbonylamino; arylalkylcarbonylamino; arylcarbonylamino; alkyloxycarbonylamino; aminocarbonylamino; mono- or di(arylalkyl)aminocarbonylamino; and alkylsulphonylalkylaminocarbonylamino; wherein two $R^3$-radicals may form together a bivalent radical selected from the group consisting of —$CR^5R^5$—$CR^5R^5$—O— (b-1)
—O—$CR^5R^5$—$CR^5R^5$— (b-2)
—O—$CR^5R^5$—$CR^5R^5$—O— (b-3)
—O—$CR^5R^5$—$CR^5R^5$—$CR^5R^5$— (b-4)
—$CR^5R^5$—$CR^5R^5$—$CR^5R^5$—O— (b-5)
—O—$CR^5R^5$—$CR^5R^5$—$CR^5R^5$—O— (b-6)
—O—$CR^5R^5$—$CR^5R^5$—$CR^5R^5$—$CR^5R^5$— (b-7)
—$CR^5R^5$—$CR^5R^5$—$CR^5R^5$—$CR^5R^5$—O— (b-8) and
—O—$CR^5R^5$—$CR^5R^5$—$CR^5R^5$—O— (b-9)

wherein $R^5$ is selected from the group of hydrogen; halo; hydroxy; alkyloxy and alkyl;

R⁴ is selected from the group consisting of hydrogen; alkyl; arylalkyl; alkyloxyalkyl; alkylcarbonyloxyalkyl; alkyloxycarbonylalkyl; arylcarbonylalkyl; alkylsulphonyloxyalkyl; aryloxyaryl; alkyloxycarbonylaryl; alkylcarbonyl; arylalkylcarbonyl; alkyloxycarbonylalkylcarbonyl; arylcarbonyl; alkyloxycarbonyl; aryloxycarbonyl; arylalkyloxycarbonyl; mono- or di(alkyl)amino-carbonyl; mono- or di(aryl)aminocarbonyl; mono- or di(arylalkyl)amino-carbonyl; mono- or di(alkyloxycarbonylalkyl)aminocarbonyl; alkyloxyalkylaminocarbonyl; mono-, di- or tri(alkyl)amidino; mono-, di- or tri(aryl)amidino; mono-, di- or tri(arylalkyl)amidino; alkylsulphonyl; arylalkylsulphonyl and arylsulphonyl;

each R¹⁰ is independently from each other, alkyl or cyano;

one of A or B is benzene and the other is thiophene;

each R⁹ is, independently from each other, selected from the group consisting of hydrogen; halo; cyano; hydroxy; carboxyl; nitro; amino; mono- or di(alkyl)amino; alkylcarbonylamino; aminosulfonyl; mono- or di(alkyl)aminosulfonyl; alkyl; alkenyl; alkyloxy; alkylcarbonyl and alkyloxycarbonyl;

X and Y are independently selected from this group consisting of O and SO₀₋₂ aryl is phenyl or naphthyl, each optionally substituted with 1, 2 or 3 substituents selected from the group consisting of halo; nitro; cyano; hydroxy; alkyloxy and alkyl;

alkyl is selected from the group consisting of a straight or branched saturated hydrocarbon radical having from 1 to 10 carbon atoms, a cyclic saturated hydrocarbon radical having from 3 to 8 carbon atoms and a saturated hydrocarbon radical containing a straight or branched moiety having from 1 to 10 carbon atoms and a cyclic moiety having from 3 to 8 carbon atoms; each radical optionally substituted with one or more substituents selected from the group consisting of halo; cyano; oxo; hydroxy; formyl; carboxyl and amino radicals;

alkenyl is selected from the group consisting of a straight or branched unsaturated hydrocarbon radical having from 1 to 6 carbon atoms, and a cyclic unsaturated hydrocarbon radical having from 3 to 6 carbon atoms; said radical having one or more double bonds and said radical being optionally substituted with one or more substituents selected from the group consisting of halo; cyano; oxo; hydroxy; formyl; carboxyl and amino radicals; and halo is selected from the group consisting of fluoro; chloro; bromo and iodo.

2. Compound according to claim 1, wherein R¹ and R² each, independently from each other, are selected from the group consisting of hydrogen and alkyl, each alkyl radical optionally substituted with hydroxy; or R¹ and R² taken together with the nitrogen atom to which they are attached, to form a radical of Formula (a-3) or (a-5), wherein m=an integer, equal to 1 or 2.

3. The compound of claim 1 wherein X is S.

4. The compound of claim 1 wherein Y is O.

5. The compound of claim 1 wherein Y is selected from the group consisting of, O, S, S(=O), or S(=O)₂.

6. Pharmaceutical composition comprising a pharmaceutically acceptable carrier or diluent and, as active ingredient, a therapeutically effective amount of a compound according to claim 1.

7. Process for the preparation of a compound according to Formula (I), characterized by N-alkylating an intermediate of Formula (II), wherein R⁹, i, j, ring A, ring B and X all have the meaning as defined in Formula (I) and wherein W represents a suitable leaving group, with an amine of Formula HNR¹R², wherein R¹ and R² are defined as in Formula (I), in a reaction-inert solvent and optionally in the presence of a suitable base;

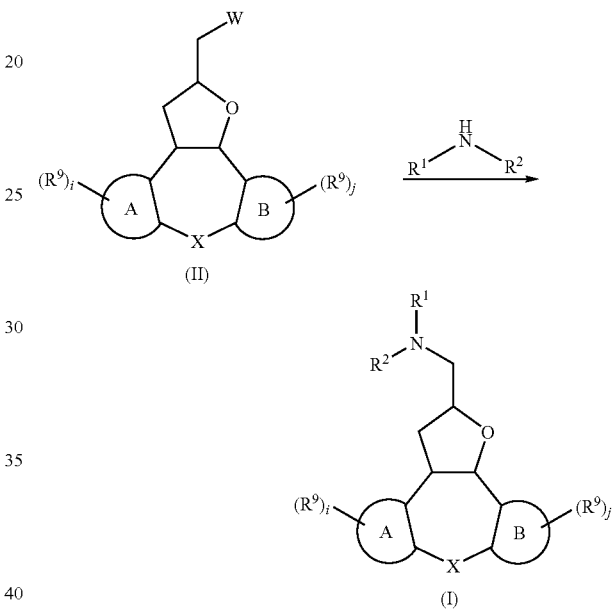

optionally, converting compounds of Formula (I) into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; N-oxides thereof and quaternary ammonium salts thereof.

* * * * *